(12) United States Patent
Miyakawa

(10) Patent No.: US 12,723,226 B2
(45) Date of Patent: Sep. 1, 2026

(54) MULTI-LAYER CELL CULTURE CONTAINER

(71) Applicant: Hiroyuki Miyakawa, Takarazuka (JP)

(72) Inventor: Hiroyuki Miyakawa, Takarazuka (JP)

( * ) Notice: Subject to any disclaimer, the term of this patent is extended or adjusted under 35 U.S.C. 154(b) by 427 days.

(21) Appl. No.: 18/396,057

(22) Filed: Dec. 26, 2023

(65) Prior Publication Data

US 2025/0207075 A1 Jun. 26, 2025

(51) Int. Cl.
*C12M 1/00* (2006.01)

(52) U.S. Cl.
CPC ............ *C12M 23/34* (2013.01); *C12M 23/02* (2013.01); *C12M 23/38* (2013.01)

(58) Field of Classification Search
CPC ... C12N 15/8273; C12M 23/02; C12M 23/34; C12M 23/38; C12M 27/12; B41J 19/20
See application file for complete search history.

(56) References Cited

U.S. PATENT DOCUMENTS

| | | | |
|---|---|---|---|
| 4,317,886 | A | 3/1982 | Johnson et al. |
| 5,010,013 | A | 4/1991 | Serkes et al. |
| 2017/0029756 | A1 | 2/2017 | Nagaike et al. |

*Primary Examiner* — Lydia Edwards

(74) *Attorney, Agent, or Firm* — LEX IP MEISTER, PLLC

(57) ABSTRACT

A cell culture container is provided. The cell culture container has a multilayer structure inside the cell culture vessel. Therefore, the number of cells obtained per occupied volume is greatly improved and efficient mass cell culture can be achieved. Further, a cap for closing the opening has or is connected with a valve capable of injecting arbitrary gas or liquid while preventing contamination of bacteria, etc., so that the gas phase inside any cell culture vessel can be easily replaced.

8 Claims, 20 Drawing Sheets

MULTI-LAYER CELL CULTURE CONTAINER

TECHNICAL FIELD

The present disclosure relates to a container for cell culture.

BACKGROUND

Most commonly used containers for cell culture are multi-well plates or T-flasks. Culture containers based on T-flasks have been developed by various manufacturers, and there are a wide range of options and readily available containers for large-scale cell culture.

However, there are few options other than these containers. Especially, there are limited options for rotational cell culture. Roller bottles are the most practical option, and other than that, octagonal column cell culture vessels (US2017/0029756 [PCT/JP2015/061152, WO2015/156367]) exist. However, these containers are not appropriate for large-scale culture.

US2017/0029756 provides a container in which the proliferation of adherent mammalian cells is performed exclusively on the inner surface of the container. In other words, the inner surface of the container only serves as a scaffold for cell growth and attachment. The area of the inner surface on which the mammalian cells are attached may be increased only when the size of the container is increased.

U.S. Pat. No. 5,010,013 suggests making the container accordion-like to increase the internal surface area. However, this method is also not enough to support large-scale cultivation and has its own demerits.

SUMMARY

An embodiment may provide a cell culture container that comprises an outer body of a polygonal prism with an internal space; a lower cover connected to a lower end of the outer body and covering a lower side of the outer body; a first inner layer structure of a polygonal prism with an internal space, wherein the first inner layer structure is disposed in the internal space of the outer body with a space from the outer body; an upper cover connected to an upper end of the outer body, wherein the upper cover has an opening and covers the upper side of the outer body; and a cap configured to close the opening of the upper cover.

The cell culture container according to an embodiment is equipped with at least one inner layer structure. Accordingly, the cell culture container may be provided with enough internal surface area for large-scale cultivation.

The cell culture container may further comprise a second inner layer structure of a polygonal prism with an internal space, wherein the second inner layer structure is disposed in the internal space of the first inner layer structure with a space from the first inner layer structure.

The cell culture container may further comprise first upper spacers provided at an upper end of the first inner layer structure and at corners of the polygonal prism of the first inner layer structure.

The cell culture container may further comprise first lower spacers provided at a lower end of the first inner layer structure and at corners of the polygonal prism of the first inner layer structure.

The cell culture container may further comprise second upper spacers provided at an upper end of the second inner layer structure and at corners of the polygonal prism of the second inner layer structure.

The cell culture container may further comprise second lower spacers provided at a lower end of the second inner layer structure and at corners of the polygonal prism of the second inner layer structure.

The cell culture container may further comprise a cover support on an internal surface of the lower cover, wherein the cover support supports a lower end of the first inner layer structure.

The cell culture container may further comprise an inner layer support connected to the lower end of the first inner layer structure, wherein the inner layer support supports a lower end of the second inner layer structure.

The first upper spacers and the first lower spacers may have an angled end surface to fit into inner corners of the outer body. 10.

The second upper spacers and the second lower spacers may have an angled end surface to fit into inner corners of the first inner layer structure.

The upper cover may comprise a neck portion with the opening and an external thread and a shoulder portion covering the upper side of the outer body, and the cap may comprise an internal thread to combine with the external thread of the upper cover and a first valve for access to an internal space of the cell culture container.

The cap may comprise a second valve for access to an internal space of the cell culture container.

The first valve and the second valve may include a split-septum.

The outer body, the first inner layer structure, and the second inner layer structure may be coaxial hexagonal prisms.

The outer body, the first inner layer structure and the second inner layer structure may respectively have six quadrangle flat panels, and width of each of the six quadrangle flat panels may decrease from the upper end to the lower end.

An embodiment may provide a cap for a cell culture container that comprises a top plate; a circumferential panel connected to the top plate along a circumference of the top plate and including an internal thread; and a first valve disposed on the top plate, wherein the first valve is normally closed and is open by an injection device.

The cap for a cell culture container according to an embodiment may provide convenient injection of any gas or liquid without contamination by applying at least one valve.

The cap may further comprise a second valve disposed on the top plate, wherein the second valve is normally closed and is open by an injection device.

The first valve and the second valve may include a split-septum.

The first valve and the second valve may be open when the injection device is pushed in.

DETAILED DESCRIPTION

Figure 1:
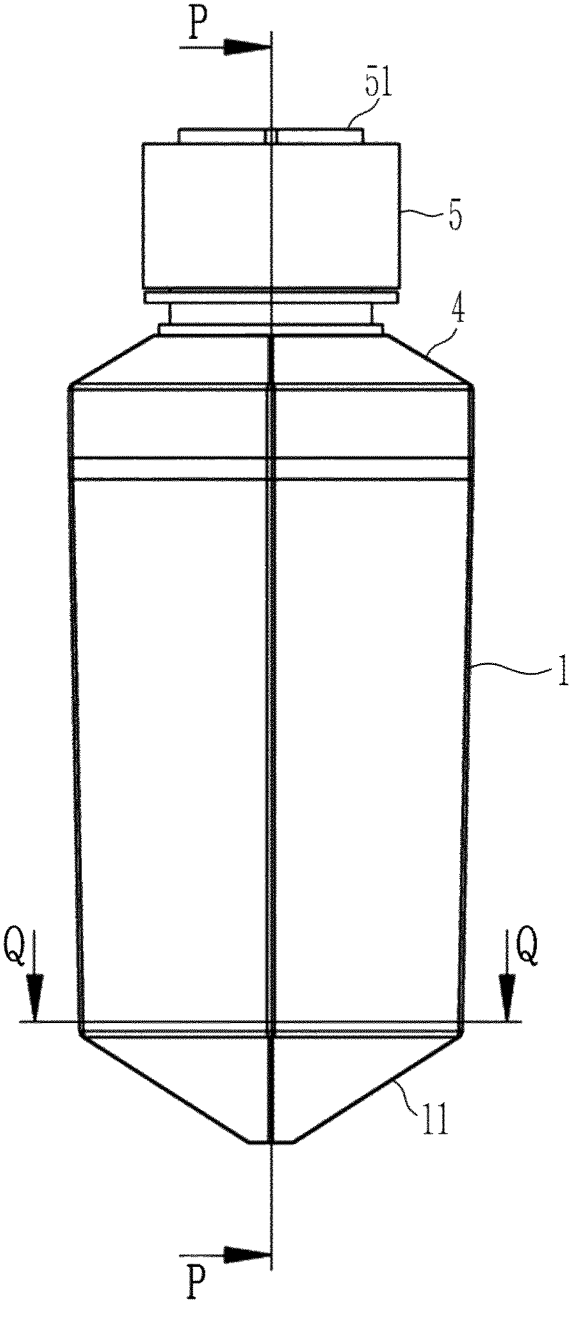
FIG. 1 shows a front view of a cell culture container according to an embodiment.

The embodiments will be described more fully hereinafter with reference to the accompanying drawings. As those skilled in the art would realize, the described embodiments may be modified in various different ways, all without departing from the spirit or scope of the present disclosure.

The drawings and the descriptions are to be considered as illustrative and not as restrictive. Throughout the specification, the same reference numbers indicate the same constituent elements.

The size and thickness of each configuration shown in the drawings are arbitrarily shown for better understanding and ease of description unless otherwise described, and the present disclosure is not limited thereto. For example, when a specific size or position relationship among elements is described with reference to a drawing, the drawing is intended to show such a size or position relationship. The thicknesses of layers, plates, panels, regions, etc., may be exaggerated for clarity unless otherwise described. For example, when a specific thickness relationship among elements is described with reference to a drawing, the drawing is intended to show such a thickness relationship. The thicknesses of some layers and areas may be exaggerated.

The singular forms are intended to include the plural forms as well, unless the context clearly indicates otherwise.

In the specification and the claims, the term "and/or" is intended to include arbitrary combinations of the terms "and" and "or" for the purposes of meaning and interpretation. For example, the expression of "A and/or B" may be understood to signify "A, B, or A and B".

In the specification and claims, the phrase "at least one of" is intended to include the meaning of "at least one selected from the group of," for the purpose of meaning and interpretation. For example, "at least one of A and B" may be understood to signify "A, B, or A and B".

Terms such as first, second, and the like will be used only to describe various constituent elements, and are not to be interpreted as limiting these constituent elements. The terms are only used to differentiate one constituent element from other constituent elements. For example, a first constituent element could be termed a second constituent element, and similarly, a second constituent element could be termed as a first constituent element, without departing from the scope of the present disclosure.

When an element, such as a layer, a plate, a panel, a region, or a substrate is described to be "above" another element, it may be directly above another element or there may be an intermediate element. In contrast, when a first element is described to be "directly above" a second element, there is no intermediate element. Throughout the specification, the term "above" a target must be "understood as being disposed above or below the target element, and does not necessarily signify "above" with respect to an opposite direction of gravity.

For example, spatially relative terms "below" or "above" may be used to facilitate the description of the relationship of one element or a constituent element to other constituent elements as shown in the drawings. The spatially relative terms are intended to include other directions in use or operation in addition to the directions shown in the drawings. For example, when the device shown in the drawing is flipped, the device disposed below another device may be disposed "above" the other device. Therefore, the exemplary term "below" may include lower and upper positions. The device may also be oriented in other directions, the spatially relative term may be analyzed differently depending on the directions.

When an element (or region, layer, portion, etc.) is described to be "connected" or "combined" to another element in the specification, it may be directly disposed, connected, or combined on the above-noted other element, or an element may be disposed therebetween.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Figure 2:
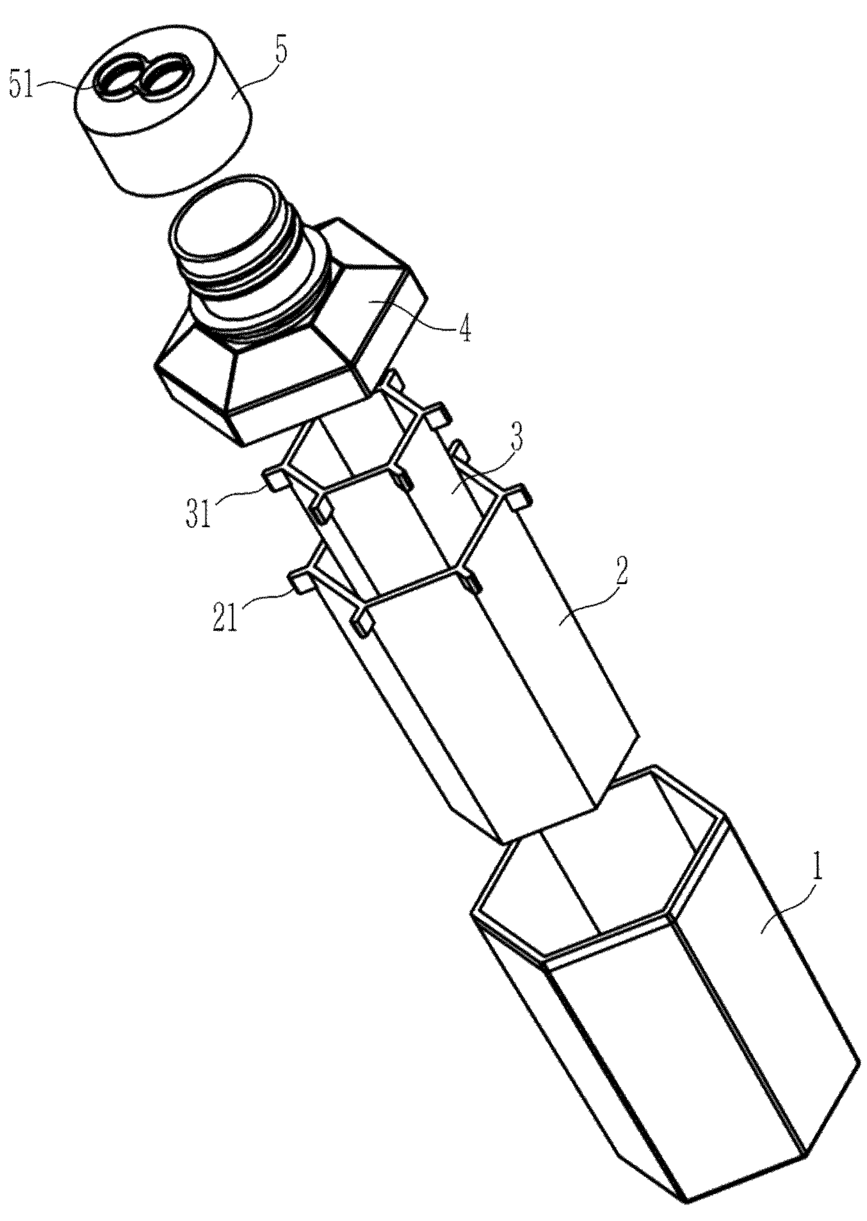
FIG. 2 shows an exploded perspective view of a cell culture container according to an embodiment.
Figure 3:
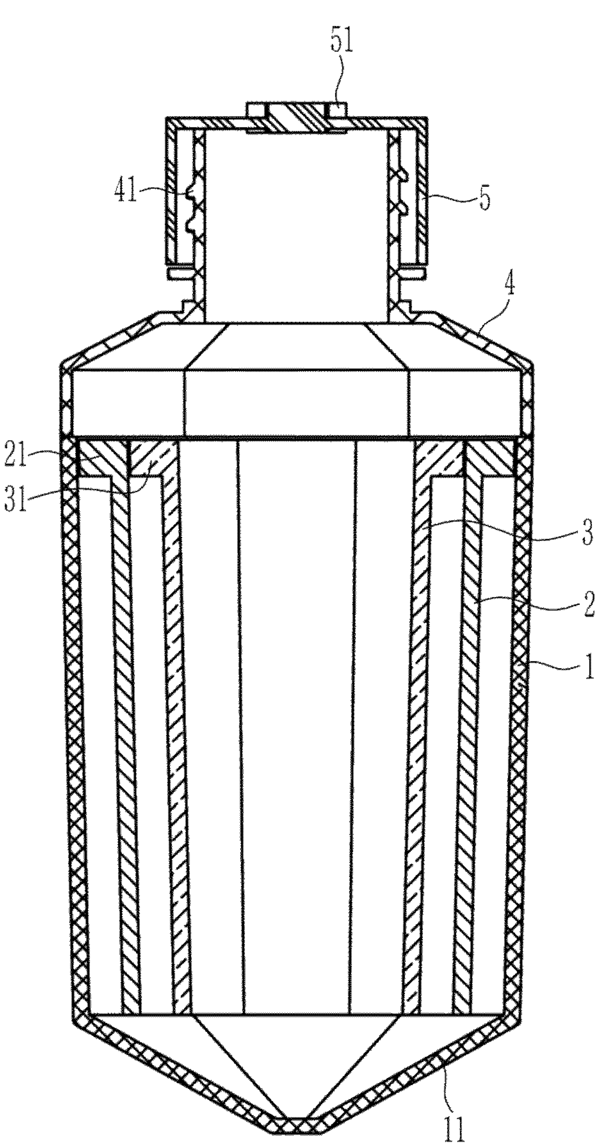
FIG. 3 shows a cross-sectional view of a cell culture container taken along line P-P of FIG. 1.
Figure 4:
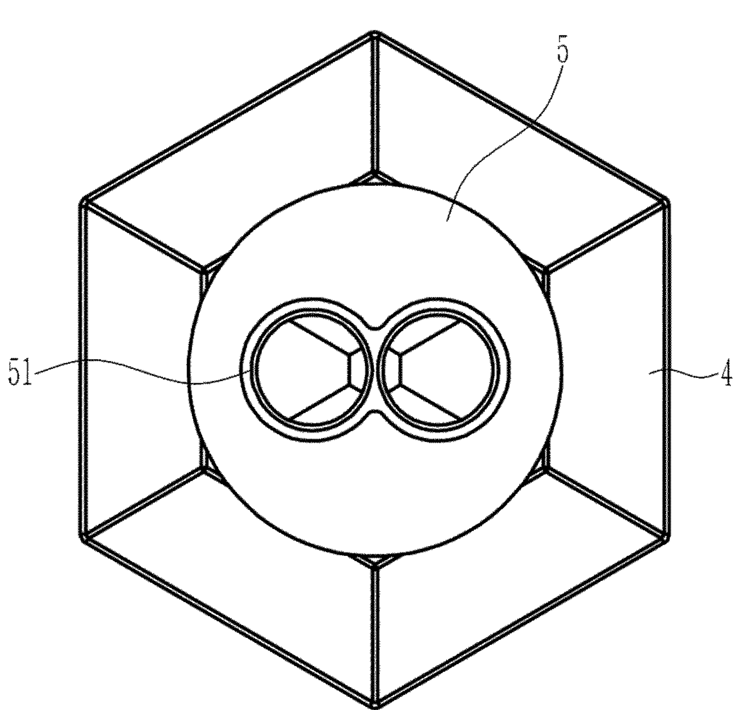
FIG. 4 shows a top view of a cell culture container according to an embodiment.
Figure 5:
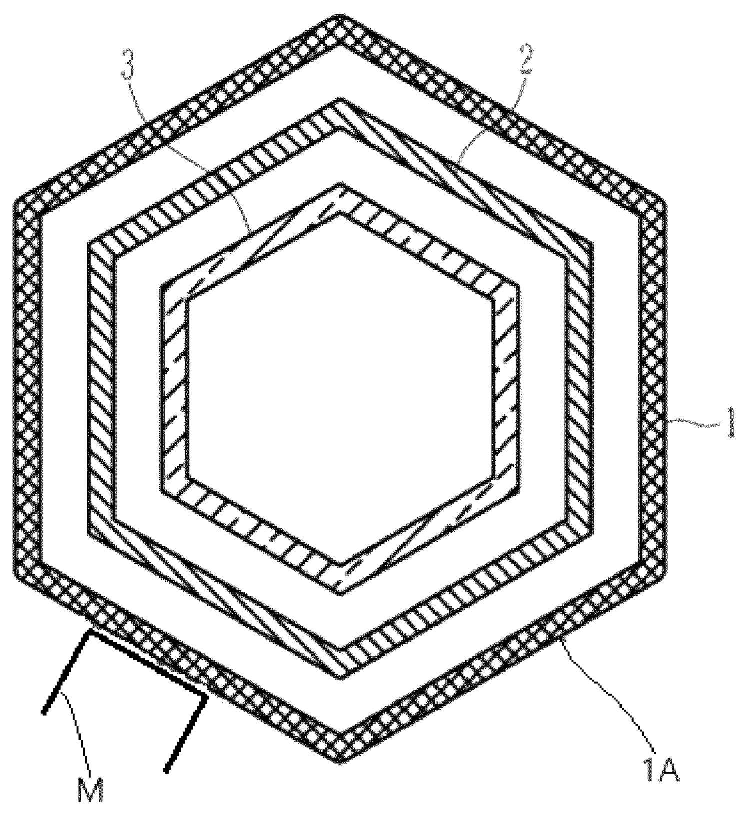
FIG. 5 shows a cross-sectional view of a cell culture container taken along line Q-Q of FIG. 1.

FIG. 1 shows a front view of a cell culture container according to an embodiment. FIG. 2 shows an exploded perspective view of a cell culture container according to an embodiment. FIG. 3 shows a cross-sectional view of a cell culture container taken along line P-P of FIG. 1. FIG. 4 shows a top view of a cell culture container according to an embodiment. FIG. 5 shows a cross-sectional view of a cell culture container taken along line Q-Q of FIG. 1.

Referring to FIGS. 1-5, the cell culture container according to an embodiment includes an outer body 1, inner layer structures 2 and 3, an upper cover 4, a lower cover 11 and a cap 5.

The outer body 1 is a polygonal prism with empty internal space. Accordingly, the outer body 1 has a plurality of quadrangle flat panels. In this embodiment, the outer body 1 has six quadrangle flat panels. The width of the quadrangle flat panels may gradually decrease from the upper end to the lower end. Accordingly, the horizontal sectional area (measured in the Q-Q direction) of the outer body 1 may gradually decrease from the upper end to the lower end. Here, the term "horizontal" is based only on the direction shown in FIG. 1 and is not intended to refer to the direction in use or operation of the cell culture container. In this embodiment, the outer body 1 is hexagonal prism but is not limited thereto. In some embodiments, the outer body 1 may be a various polygonal prism, such as a pentagonal prism or an octagonal prism. The outer body 1 may be made of various materials such as plastic or glass and may be transparent, colored, or opaque. These materials may be selected to ensure transparency. However, it is also possible to use opaque resins that can block light, depending on the cultivation conditions. Additionally, materials that selectively absorb or transmit specific wavelength ranges may be employed. As mentioned above, the outer body 1 may be hexagonal or polygonal, but it is effective to configure the outer body 1 to have at least a flat panel 1A on a flat surface, so that the inner surface to which mammalian cells adhere can be observed under a microscope M (shown in FIG. 5 with a single dotted line) while observing the culture state of cells inside to determine whether to continue culture. This is because if the outer body were to be cylindrical, without the flat panel 1A, it would be difficult to observe the state of culture with the microscope M during the course of culture.

The outer body 1 is connected to the lower cover 11 at the lower end. The lower cover 11 may have a conical shape or a polygonal cone shape. The lower side of the outer body 1 is closed by the lower cover 11. The lower cover 11 may be made of various materials such as plastic or glass and may be transparent, colored, or opaque. The lower cover 11 may be integrally formed with the outer body 1.

The inner layer structures 2 and 3 are polygonal prisms with empty internal space. Accordingly, the inner layer structures 2 and 3 have a plurality of quadrangle flat panels. In this embodiment, the inner layer structures 2 and 3 respectively have six quadrangle flat panels. The width of the quadrangle flat panels may gradually decrease from the upper end to the lower end. Accordingly, the horizontal sectional area (measured in the Q-Q direction) of the inner layer structures 2 and 3 may gradually decrease from the upper end to the lower end.

The inner layer structures 2 and 3 may have the same rotational axis with the outer body 1. In other words, the inner layer structures 2 and 3 and the outer body 1 may be coaxial prisms. In this embodiment, the inner layer structures 2 and 3 are hexagonal prisms but are not limited thereto. In some embodiments, the inner layer structures 2 and 3 may be a various polygonal prism, such as a pentagonal prism or an octagonal prism. The inner layer structures 2 and 3 may have the same polygonal shape with the outer body 1 but are not limited thereto.

The inner layer structures 2 and 3 have upper spacers 21 and 31.

In this embodiment, the first upper spacers 21 are provided at the upper end of the first inner layer structure 2 and at the respective corners of the polygonal prism of the first inner layer structure 2, but are not limited thereto. The first upper spacers 21 may be provided at some corners, not all, of the polygonal prism of the first inner layer structure 2 or at middle portions, not at the corners, of the quadrangle flat panels of the first inner layer structure 2. The first upper spacers 21 may be provided at a middle portion, not at the upper end, of the first inner layer structure 2. The first upper spacers 21 may have an angled end surface so that they fit into the inner corners of the outer body 1. The first upper spacers 21 may fix the first inner layer structure 2 to the outer body 1 with a space therebetween.

In this embodiment, the second upper spacers 31 are provided at the upper end of the second inner layer structure 3 and at the respective corners of the polygonal prism of the second inner layer structure 3, but are not limited thereto. The second upper spacers 31 may be provided at some corners, not all, of the polygonal prism of the second inner layer structure 3 or at middle portions, not at the corners, of the quadrangle flat panels of the second inner layer structure 3. The second upper spacers 31 may be provided at a middle portion, not at the upper end, of the second inner layer structure 3. The second upper spacers 31 may have an angled end surface so that they fit into the inner corners of the first inner layer structure 2. The second upper spacers 31 may fix the second inner layer structure 3 to the first inner layer structure 2 with a space therebetween.

When the spacers 21 and 31 are located at the corners of the polygonal prism, an observation area of the adhesive surface may be widely secured and generation of uneven cell adhesion due to the liquid flow during rotational cultivation may be reduced.

In this embodiment, the number of the inner layer structures 2 and 3 is two but is not limited thereto. In some embodiments, the cell culture container may include one inner layer structure, or equal to or more than three inner layer structures.

The inner layer structures 2 and 3 may be made of various materials such as plastic or glass and may be transparent, colored, or opaque. These materials may be selected to ensure transparency. However, it is also possible to use opaque resins that can block light, depending on the cultivation conditions. Additionally, materials that selectively absorb or transmit specific wavelength ranges may be employed.

The upper cover 4 is connected to the upper end of the outer body 1. The upper cover 4 may be connected to the upper end of the outer body 1 with an adhesive, by a welding or by a mechanical combining.

The upper cover 4 includes a neck portion with an opening and an external thread for connection to the cap 5, and a shoulder portion covering the upper side of the outer body 1. The upper cover 4 may prevent the inner layer structures 2 and 3 from getting out of the outer body 1 and fix the inner layer structures 2 and 3 in the outer body 1.

The cap 5 is provided with an internal thread to combine with the external thread of the neck portion of the upper cover 4. The cap 5 may be screwed to the neck portion of the upper cover 4 to close the opening of the upper cover 4 and to seal the cell culture container. The cap 5 may be unscrewed from the neck portion of the upper cover 4 to open the cell culture container.

The cap 5 may be provided with valves 51 that allows convenient injection of any gas or liquid into the cell culture container while preventing contamination of foreign substances such as bacteria. This enables the convenient replacement of the internal atmosphere of the cell culture container. The valves 51 may be connected to the cap 5 by various method such as an insert molding, a luer-lock, or a luer-slip. The valves 51 may be made of isoprene, silicone, combination thereof, or similar materials.

In this embodiment, the cap 5 includes two valves 51 but is not limited thereto. In some embodiments, the cap 5 may includes one valve, or equal to or more than three valves. When the cap 5 has two or more valves 51, through one valve, gases or liquids may be introduced from the outside, while through another valve, gases or liquids within the cell culture container may be withdrawn. For replacement of the internal atmosphere of the cell culture container, a continuous injection of gas through a membrane filter into the cell culture container, along with the simultaneous periodic expulsion of gas from the inside of the cell culture container may be performed. In addition, when adding supplements or cell suspensions to the culture medium during cultivation, the use of valves 51 without opening the cap may provide much cleaner operations with a reduced risk of contamination.

The internal thread on the cap 5 may be modified for a container other than the present embodiments. The cap 5 with the valves 51 may be universally used for cell culture containers by modifying the screw pitch of the internal thread and the size. In other words, the cap 5 with the valves 51 may be used not only in the rotational cultivation but also in the static cultivation using T-flasks. The cap 5 with the valves 51 may introduce gases with any desired phase and partial pressure through the valves 51. Therefore, the internal atmosphere of the cell culture container may be conveniently replaced and facilitate cultivation environments such as low-oxygen cultivation.

The cell culture container according to an embodiment is equipped with at least one inner layer structure. Accordingly, the cell culture container may be provided with enough internal surface area for large-scale cultivation. Further, the cell culture container according to an embodiment may provide convenient injection of any gas or liquid without contamination by applying a cap equipped with at least one valve.

Figure 6:
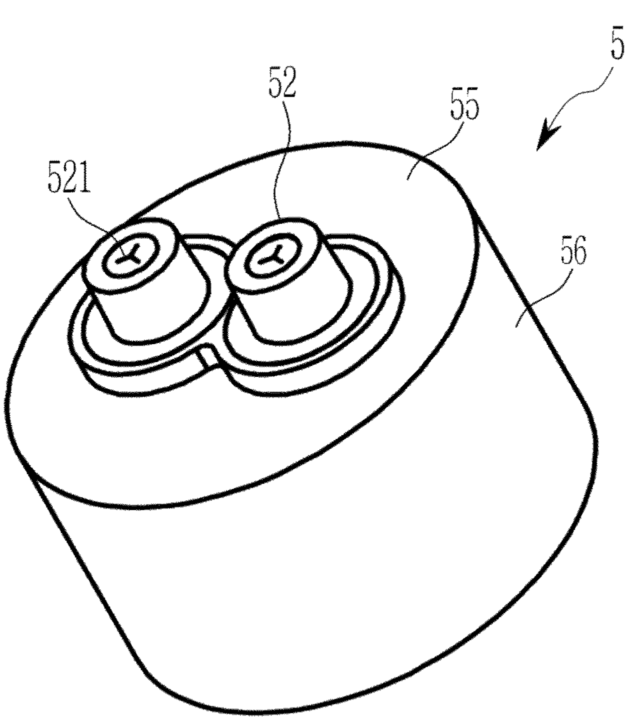
FIG. 6 shows a perspective view of a cap of a cell culture container according to an embodiment.
Figure 7:
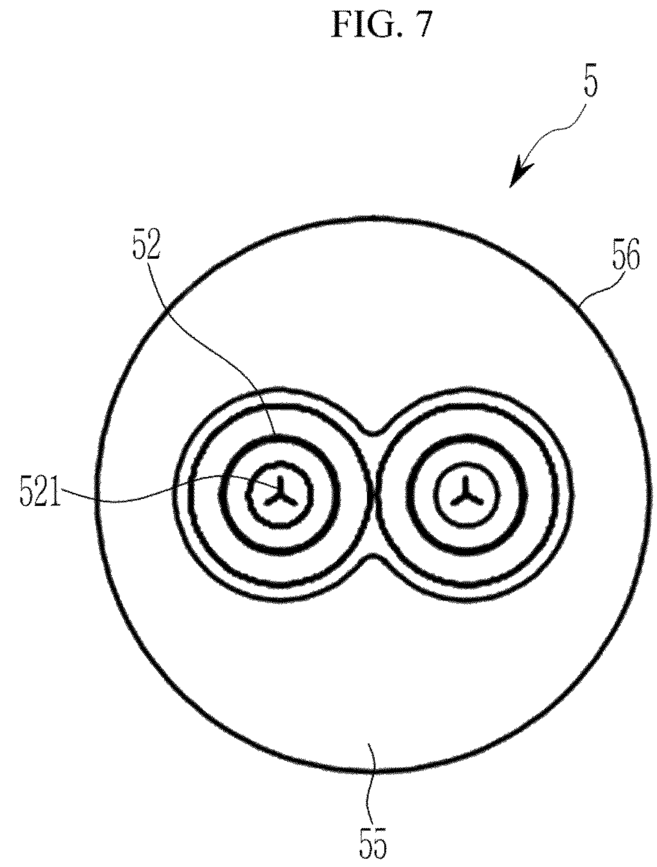
FIG. 7 shows a top view of a cap of a cell culture container according to an embodiment.
Figure 8:
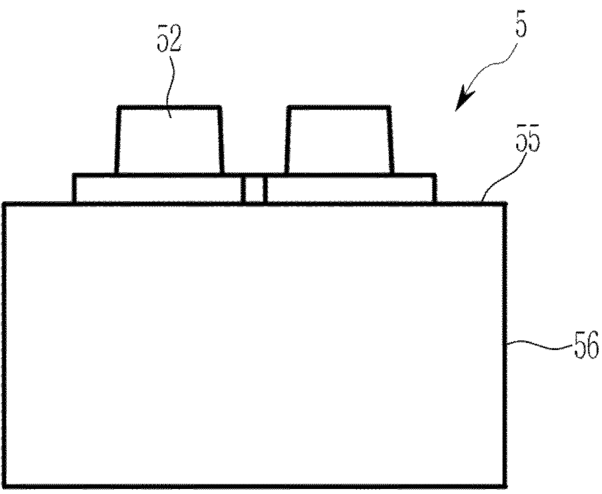
FIG. 8 shows a front view of a cap of a cell culture container according to an embodiment.
Figure 9:
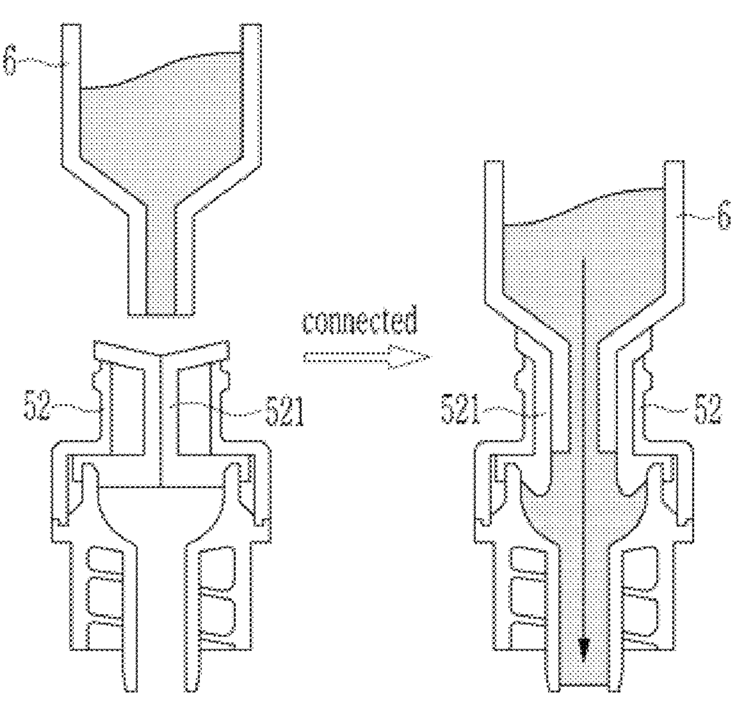
FIG. 9 is a schematic diagram showing connecting of a syringe through a valve installed on a cap of a cell culture container according to an embodiment.
Figure 10:
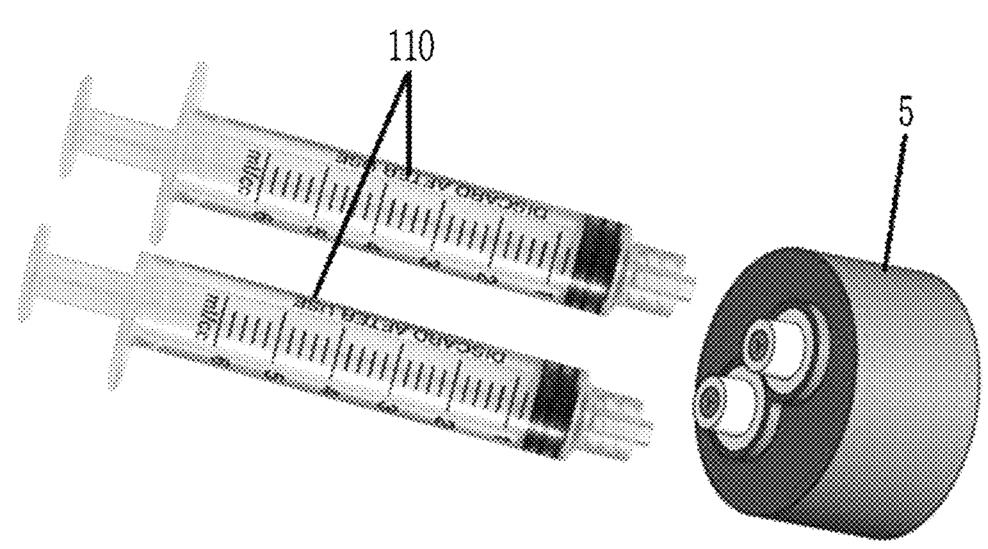
FIG. 10 is a schematic diagram showing connecting syringes with luer-lock needle hub to valves installed on a cap of a cell culture container according to an embodiment.
Figure 11:
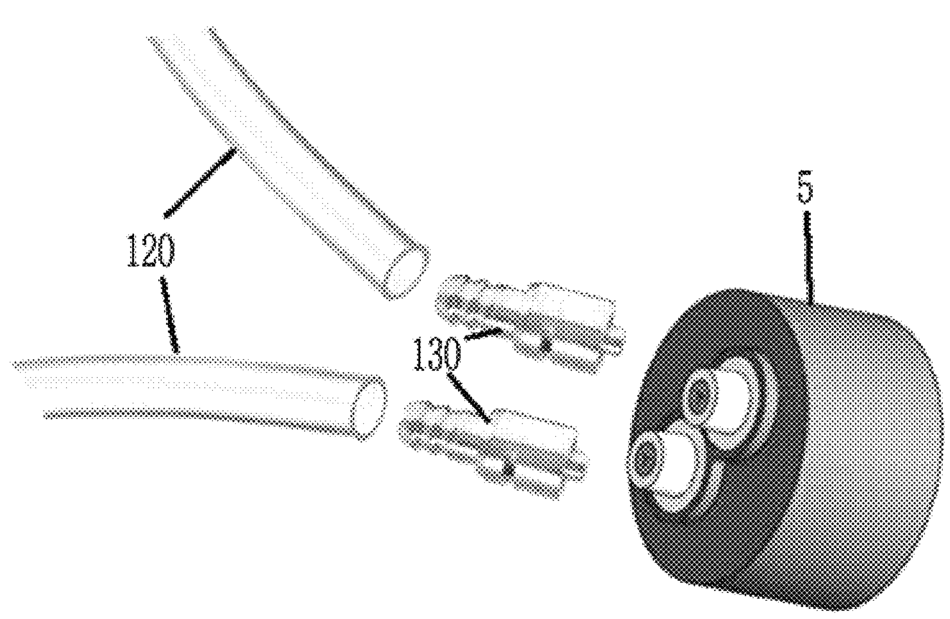
FIG. 11 is a schematic diagram showing connection of rubber tubes with lure-lock connectors to valves installed on a cap of a cell culture container according to an embodiment.
Figure 12:
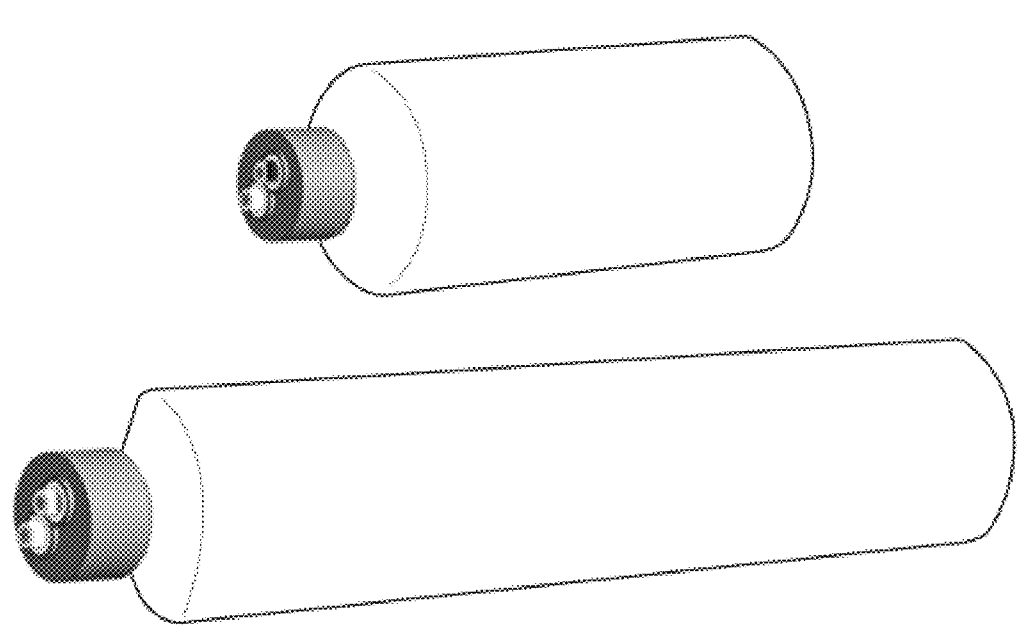
FIGS. 12-15 show examples of cell culture containers employing a cap according to an embodiment.
Figure 13:
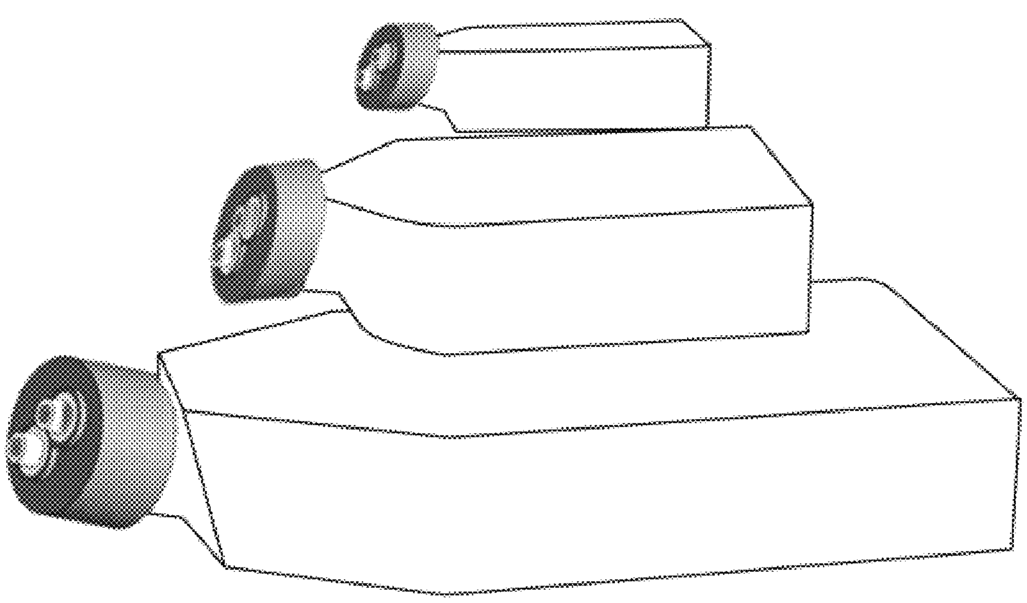
Figure 14:
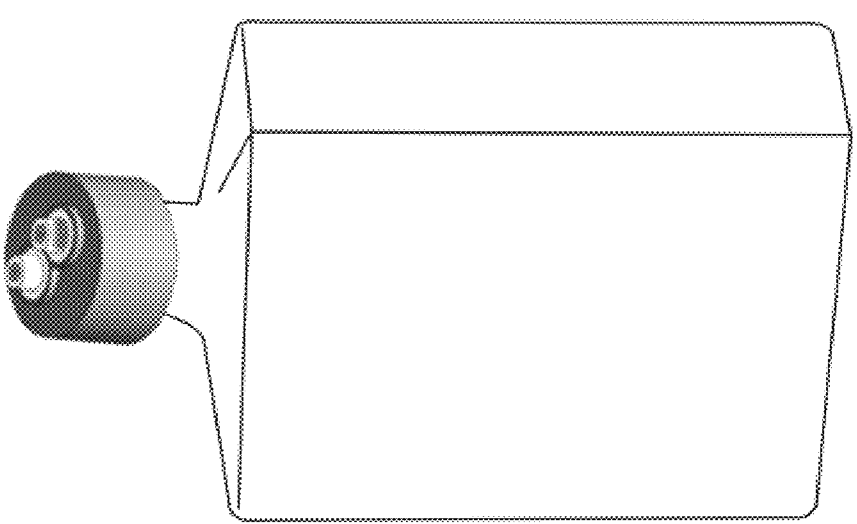
Figure 15:

The cap 5 may be provided with various types of valves. FIG. 6 shows a perspective view of a cap of a cell culture container according to an embodiment. FIG. 7 shows a top view of a cap of a cell culture container according to an embodiment. FIG. 8 shows a front view of a cap of a cell culture container according to an embodiment. FIG. 9 is a schematic diagram showing connecting of a syringe through a valve installed on a cap of a cell culture container according to an embodiment. FIG. 10 is a schematic diagram showing connecting syringes with luer-lock structure to valves installed on a cap of a cell culture container according to an embodiment. FIG. 11 is a schematic diagram showing connection of rubber tubes with lure-lock connectors to valves installed on a cap of a cell culture container according to an embodiment. FIGS. 12-15 show examples of cell culture containers employing a cap according to an embodiment.

Referring to FIGS. 6-9, the cap 5 includes a top plate 55, a circumferential panel 56 connected to the top plate 55 along a circumference of the top plate 55, and valves 52 installed on the top plate 55. The valves 52 protrude above the top plate 55 of the cap 5 and have an insertion structure 521 through which an injection device, such as a syringe needle or needle hub, is inserted. The valves 52 may employ a split-septum system or may be a mechanical valve. The valves 52 may be made of isoprene, silicone, combination thereof, or similar materials.

FIG. 9 shows the valve 52 employing an example split-septum system. The valve 52 includes a split-septum as the insertion structure 521. The split-septum 521 has a hole which is normally closed and is open when an injection device 6 is pushed in. With this system, the valve 52 may provide convenient access to the interior of the cell culture container without unscrewing the cap 5. The valve 52 may employ other known split-septum systems or mechanical valves.

Referring to FIG. 10, the valves installed on a cap of a cell culture container according to an embodiment may be connected to syringes with luer-lock needle hub. With these connections, adding small amounts of material or sampling small amounts of cultured cells may be performed without opening the cap.

Referring to FIG. 11, the valves installed on a cap of a cell culture container according to an embodiment may be connected to rubber tubes. With these connections, exchange of gasses, liquid, and etc. may be performed without opening the cap.

The cap 5 with the valves 51 may be universally used for cell culture containers by modifying the screw pitch of the internal thread and the size. FIGS. 12-15 show examples of cell culture containers employing a cap according to an embodiment. The cap 5 according to an embodiment may be applied to various type of cell culture containers.

Figure 16:
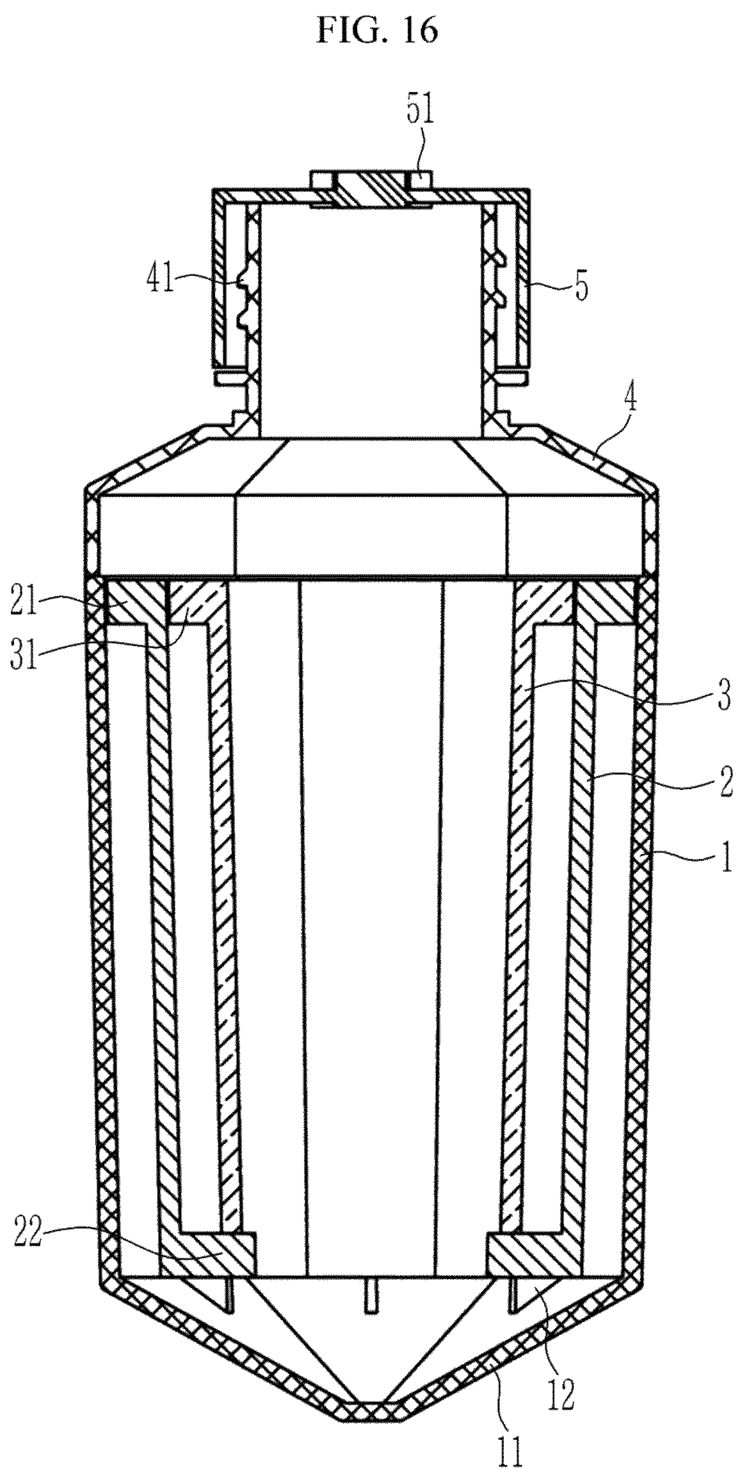
FIG. 16 shows a cross-sectional view, taken along line P-P of FIG. 1, of a cell culture container according to an embodiment.
Figure 17:
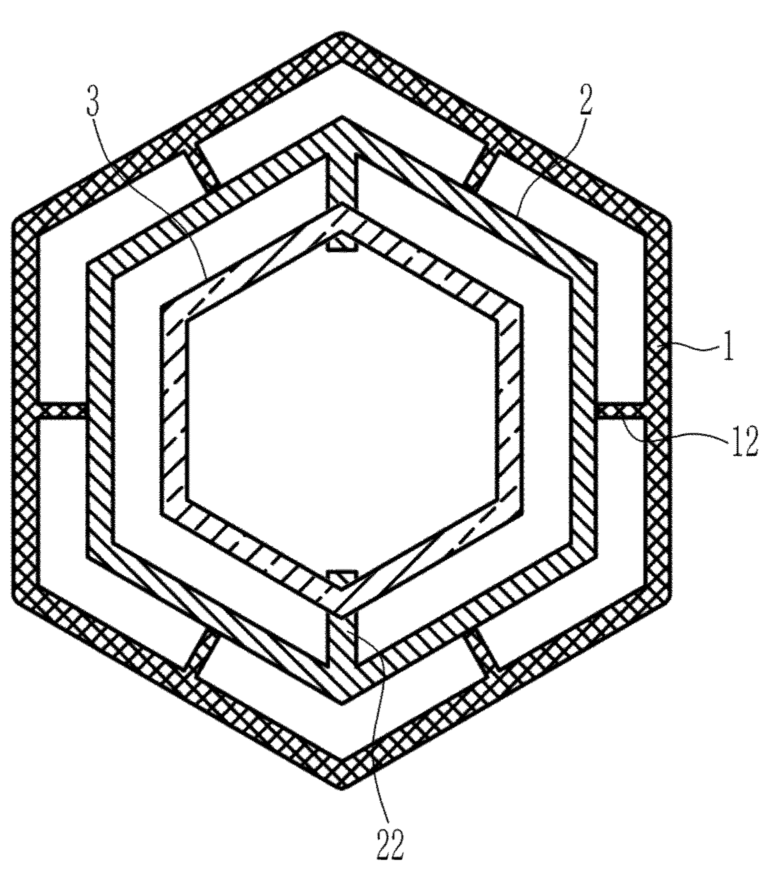
FIG. 17 shows a cross-sectional view, taken along line Q-Q of FIG. 1, of a cell culture container according to an embodiment.

FIG. 16 shows a cross-sectional view, taken along line P-P of FIG. 1, of a cell culture container according to an embodiment. FIG. 17 shows a cross-sectional view, taken along line Q-Q of FIG. 1, of a cell culture container according to an embodiment.

The cell culture container shown in FIGS. 16 and 17 is further provided with a lower supporting structure supporting the inner layer structures 2 and 3. The lower supporting structure includes cover supports 12 and inner layer supports 22. The cover supports 12 are disposed on the internal surface of the lower cover 11 and support the lower end of the first inner layer structure 2 and/or the inner layer supports 22. The inner layer supports 22 are connected to the lower end of the first inner layer structure 2 and protrude toward the rotational axis. The inner layer supports 22 support the lower end of the second inner layer structure 3. With this lower supporting structure, the inner layer structures 2 and 3 may be solidly installed in the outer body 1.

Figure 18:
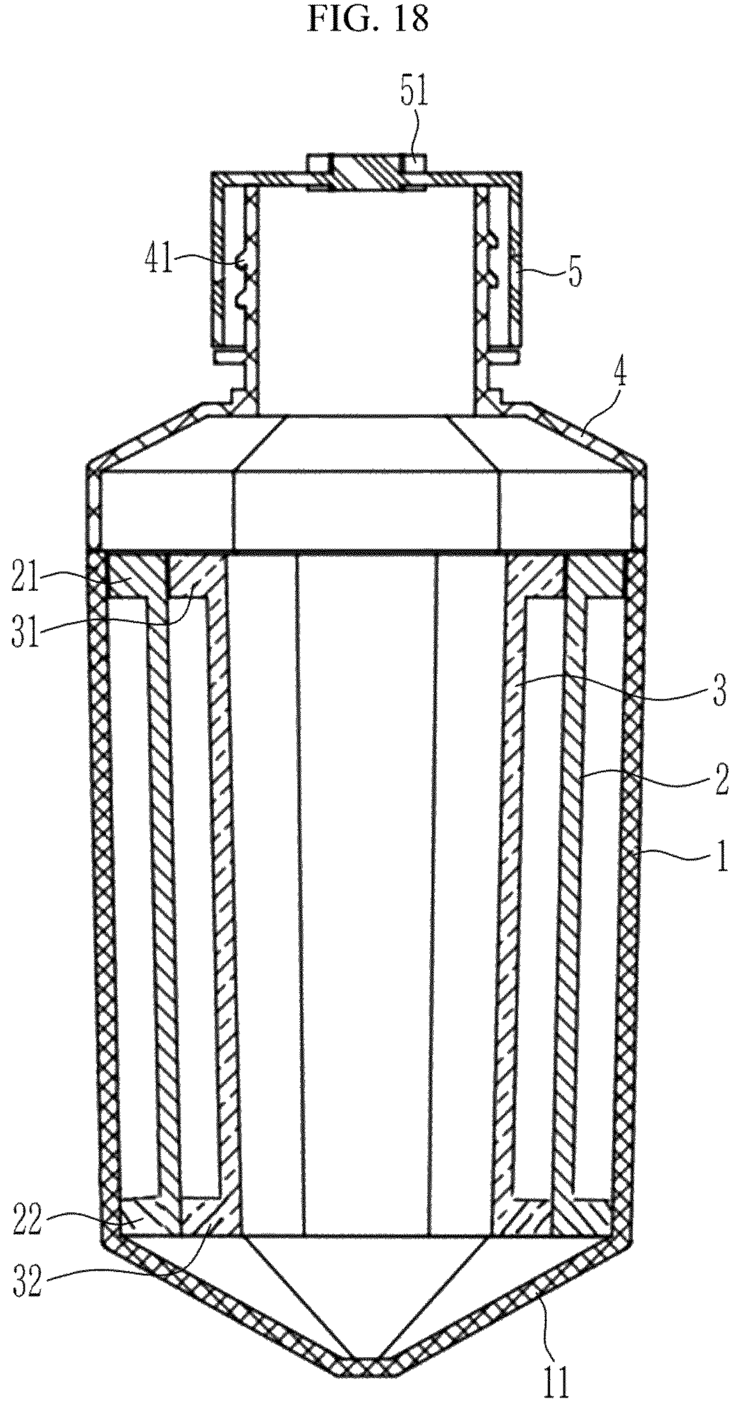
FIG. 18 shows a cross-sectional view, taken along line P-P of FIG. 1, of a cell culture container according to an embodiment.
Figure 19:
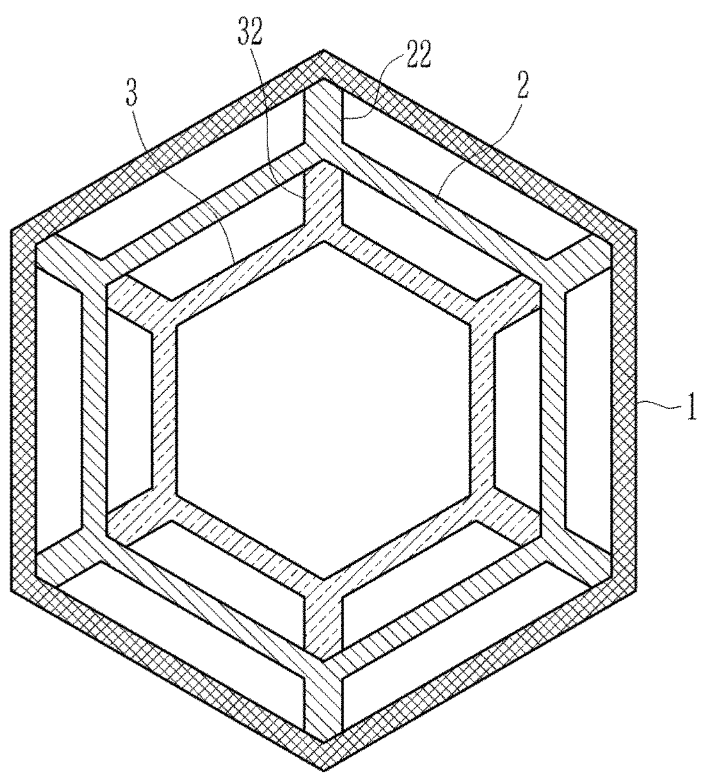
FIGS. 19-21 show cross-sectional views, taken along line Q-Q of FIG. 1, of a cell culture container according to embodiments.
Figure 20:
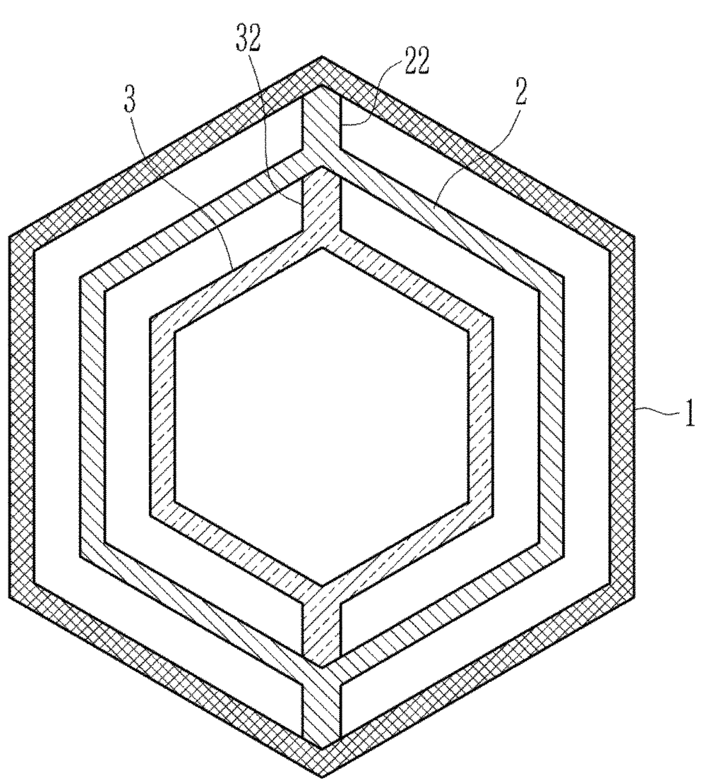
Figure 21:
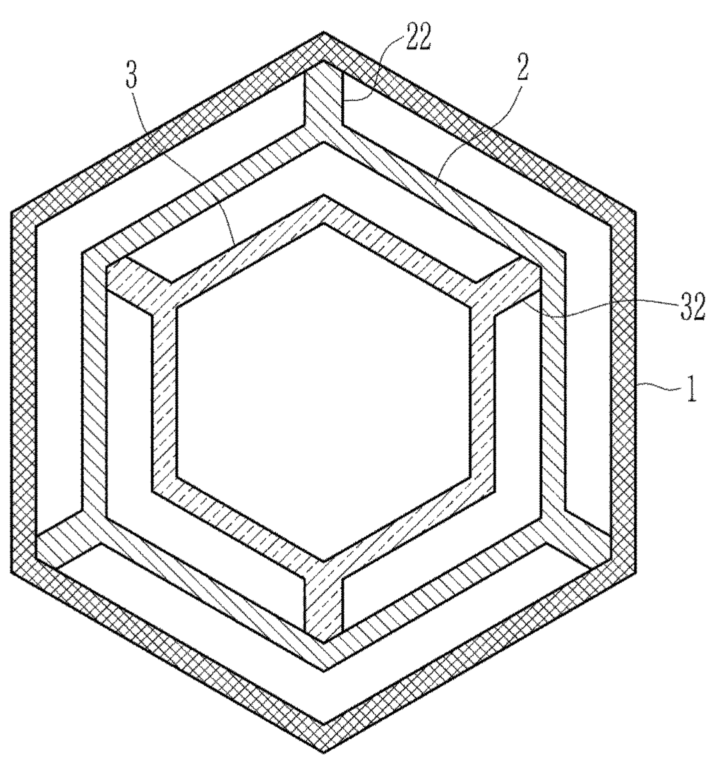

FIG. 18 shows a cross-sectional view, taken along line P-P of FIG. 1, of a cell culture container according to an embodiment. FIGS. 19-21 show cross-sectional views, taken along line Q-Q of FIG. 1, of cell culture container according to an embodiments.

The cell culture containers shown in FIGS. 18 and 19-21 are further provided with lower spacers 22 and 23.

The first lower spacers 22 are provided at the lower end of the first inner layer structure 2 and at the respective corners of the polygonal prism of the first inner layer structure 2, but are not limited thereto. The first lower spacers 22 may be provided at some corners, not all, of the polygonal prism of the first inner layer structure 2 or at middle portions, not at the corners, of the quadrangle flat panels of the first inner layer structure 2. The first lower spacers 22 may be provided at a lower middle portion, not at the lower end, of the first inner layer structure 2. The first lower spacers 22 may have an angled end surface so that they fit into the inner corners of the outer body 1. The first lower spacers 22 may fix the first inner layer structure 2 to the outer body 1 with a space therebetween along with the first upper spacers 21.

The second lower spacers 32 are provided at the lower end of the second inner layer structure 3 and at the respective corners of the polygonal prism of the second inner layer structure 3, but are not limited thereto. The second lower spacers 32 may be provided at some corners, not all, of the polygonal prism of the second inner layer structure 3 or at middle portions, not at the corners, of the quadrangle flat panels of the second inner layer structure 3. The second lower spacers 32 may be provided at a lower middle portion, not at the lower end, of the second inner layer structure 3. The second lower spacers 32 may have an angled end surface so that they fit into the inner corners of the first inner layer structure 2. The second lower spacers 32 may fix the second inner layer structure 3 to the first inner layer structure 2 with a space therebetween along with the second upper spacers 31.

FIG. 19 shows an embodiment of cell culture container provided with the first lower spacers 22 and the second lower spacers 32 at all corners. FIG. 20 shows an embodiment of cell culture container provided with the first lower spacers 22 and the second lower spacers 32 at two opposite corners. FIG. 21 shows an embodiment of cell culture container provided with the first lower spacers 22 and the second lower spacers 32 at three corners. In FIG. 21, the second lower spacers 32 may fit into the three inner corners of the first inner layer structure 3 where the first lower spacers 22 are not located.

With the lower spacers 22 and 32 and the upper spacers 21 and 23, the inner layer structures 2 and 3 may be solidly installed in the outer body 1.

The embodiments may be implemented in various different forms. It may be understood by those skilled in the art to which the present disclosure pertains that the present disclosure may be implemented in other specific forms without changing the spirit or essential features thereof. Therefore, it should be understood that the aforementioned embodiments are illustrative in terms of all aspects and are not limited.

What is claimed is:

1. A cell culture container comprising:
- a container body having a bottom and a polygonal prism-shaped internal space;
- a plurality of polygonal prism-shaped cylindrical bodies arranged coaxially within the container body;
- a lid attached to the axial end of the container body;
- a cap attached to a cylindrical neck portion of the lid;
- a plurality of spacers provided at corners on outer peripheral surfaces of the cylindrical bodies and at axial ends of the cylindrical bodies;
- wherein the spacers fit into corners of an inner peripheral surface of the container body or corners of an inner peripheral surface of the cylindrical bodies, and
- the bottom of the container body has a conical shape or a polygonal-pyramidal shape.

2. The cell culture container of claim 1, wherein the cylindrical bodies comprise a first cylindrical body and a second cylindrical body, the second cylindrical body being arranged coaxially within the first cylindrical body, and
- the spacers comprise:
- a first spacer provided at a corner on an outer peripheral surface of the first cylindrical body and at an axial end of the first cylindrical body, and
- a second spacer provided at a corner on an outer peripheral surface of the second cylindrical body and at an axial end of the second cylindrical body,
- wherein the first spacer fits into a corner of the inner peripheral surface of the container body, and the second spacer fits into a corner of the inner peripheral surface of the first cylindrical body.

3. The cell culture container according to claim 1, wherein end portions of the spacers that fits into the corners of the inner peripheral surface of the container body or the corners of the inner peripheral surface of the cylindrical body have a V-shape.

4. The cell culture container according to claim 2, wherein an end portion of the first spacer that fits into a corner of the inner peripheral surface of the container body has a V-shape, and an end portion of the second spacer that fits into a corner of the inner peripheral surface of the first cylindrical body has a V-shape.

5. The cell culture container according to claim 2, wherein the container body, the first cylindrical body, and the second cylindrical body are all hexagonal in shape, the first spacer is provided at three corners on the outer peripheral surface of the first cylindrical body and at the axial end of the first cylindrical body at equal intervals, the second spacer is provided at three corners on the outer peripheral surface of the second cylindrical body and at the axial end of the second cylindrical body at equal intervals, and the second spacer fits inside a corner of the outer peripheral surface of the first cylindrical body where the first spacer is not provided, and
- wherein the cell culture container is used to detach and disperse target cells attached to the inner surface of the container body, and both inner and outer surfaces of the first and second cylindrical bodies.

6. The cell culture container according to claim 2, wherein the length in the longitudinal direction of the first spacer in the first cylindrical body is shorter than the length in the longitudinal direction of the first cylindrical body, and a passage of an uniform gap is formed between the inner surface of the container body and the outer surface of the first cylindrical body to allow a flow of cell culture fluid.

7. The cell culture container according to claim 4, wherein the container body, the first cylindrical body, and the second cylindrical body are all hexagonal in shape, the first spacer is provided at three corners on the outer peripheral surface of the first cylindrical body and at the axial end of the first cylindrical body at equal intervals, the second spacer is provided at three corners on the outer peripheral surface of the second cylindrical body and at the axial end of the second cylindrical body at equal intervals, and the second spacer fits inside a corner of the outer peripheral surface of the first cylindrical body where the first spacer is not provided, and
- wherein the cell culture container is used to detach and disperse target cells attached to the inner surface of the container body, and both inner and outer surfaces of the first and second cylindrical bodies.

8. The cell culture container according to claim 4, wherein the length in the longitudinal direction of the first spacer in the first cylindrical body is shorter than the length in the longitudinal direction of the first cylindrical body, and a passage of an uniform gap is formed between the inner surface of the container body and the outer surface of the first cylindrical body to allow a flow of cell culture fluid.

* * * * *